(12) United States Patent
Goh

(10) Patent No.: US 7,322,963 B2
(45) Date of Patent: Jan. 29, 2008

(54) TELESCOPIC SAFETY ARTERIOVENOUS FISTULA NEEDLE

(75) Inventor: Kim Seah Goh, Singapore (SG)

(73) Assignee: JMS Singapore Pte Ltd., Singapore (SG)

( * ) Notice: Subject to any disclaimer, the term of this patent is extended or adjusted under 35 U.S.C. 154(b) by 642 days.

(21) Appl. No.: 10/718,221

(22) Filed: Nov. 20, 2003

(65) Prior Publication Data

US 2005/0113756 A1  May 26, 2005

(51) Int. Cl.
*A61M 5/178* (2006.01)

(52) U.S. Cl. .................................. 604/165.03

(58) Field of Classification Search ........... 604/165.03, 604/177, 174, 263, 198, 110, 171, 164.04, 604/264, 93.01, 111
See application file for complete search history.

(56) References Cited

U.S. PATENT DOCUMENTS

| 5,382,240 | A | * | 1/1995 | Lam ........................... 604/177 |
| 5,746,215 | A | * | 5/1998 | Manjarrez ................... 600/573 |
| 5,833,670 | A | * | 11/1998 | Dillon et al. ............... 604/263 |
| 5,928,199 | A | * | 7/1999 | Nakagami ................... 604/171 |
| 5,931,815 | A | * | 8/1999 | Liu ............................. 604/171 |
| 6,659,984 | B2 | * | 12/2003 | Maclean Crawford et al. .. 604/263 |
| 2003/0153874 | A1 | * | 8/2003 | Tal .......................... 604/164.1 |

* cited by examiner

*Primary Examiner*—Nicholas D. Lucchesi
*Assistant Examiner*—Christopher Koharski
(74) *Attorney, Agent, or Firm*—Pillsbury Winthrop Shaw Pittman LLP

(57) ABSTRACT

A telescopic intravenous infusion set and/or blood collection assembly is provided with a safety feature for covering the used needle. The safety feature is a telescopic device including a shield with handling wings, which when placed in cooperating relationship, allows accommodation of a conventional unmodified blood collection needle affixed to a hub, and a sleeve with a locking cap. After use, the hub with the needle are pulled rearwardly into positive locking position which prevent the hub and needle from moving out of the shield thereafter. The telescopic nature of the device then allows the locked needle/hub to move rearward in relation to the shield until the shield is unreleasably locked to the sleeve. The shield provides for passage of the needle and hub from a releasable locked use position to a shielded and unreleasable locked protected position.

27 Claims, 11 Drawing Sheets

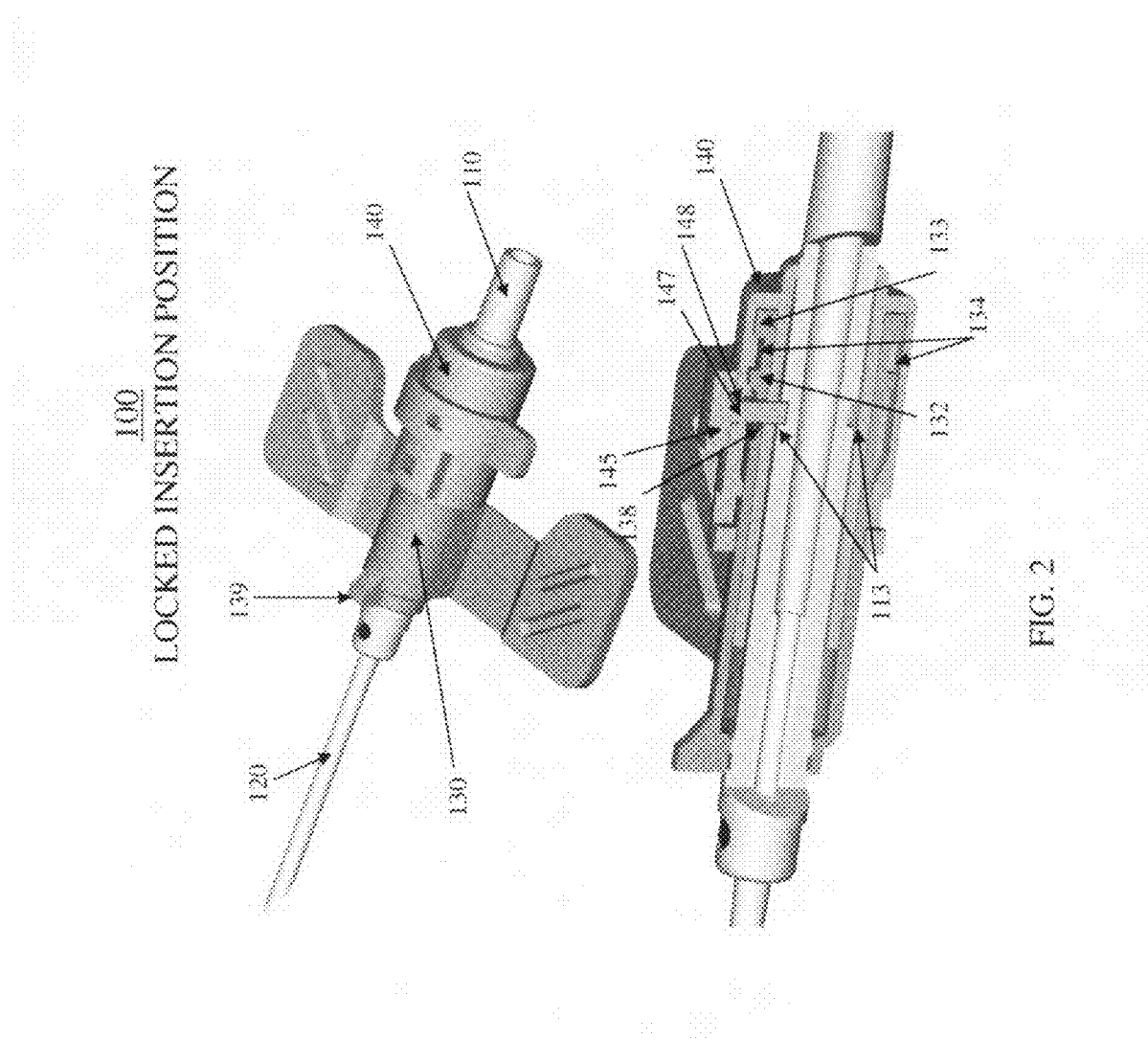

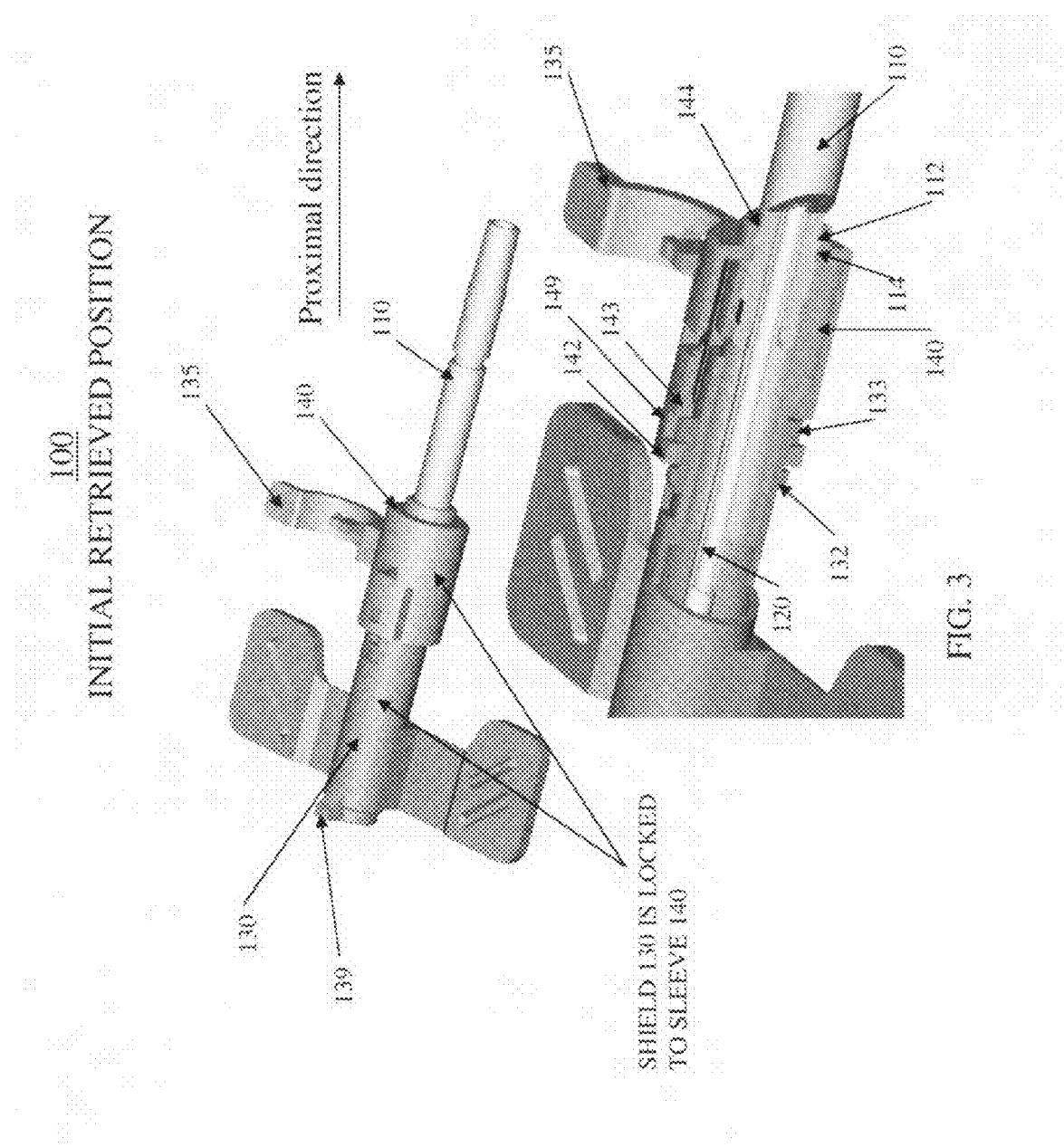

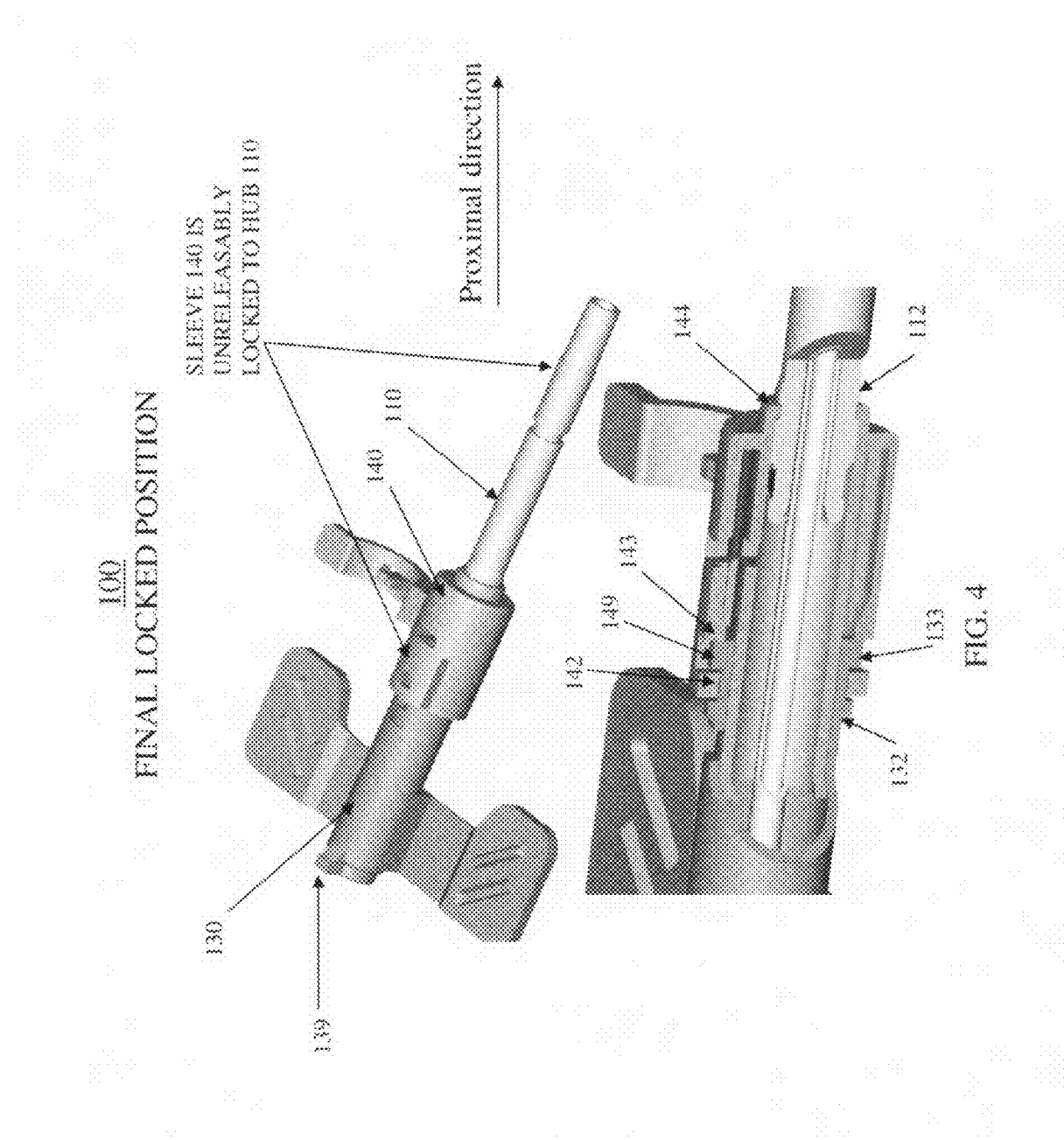

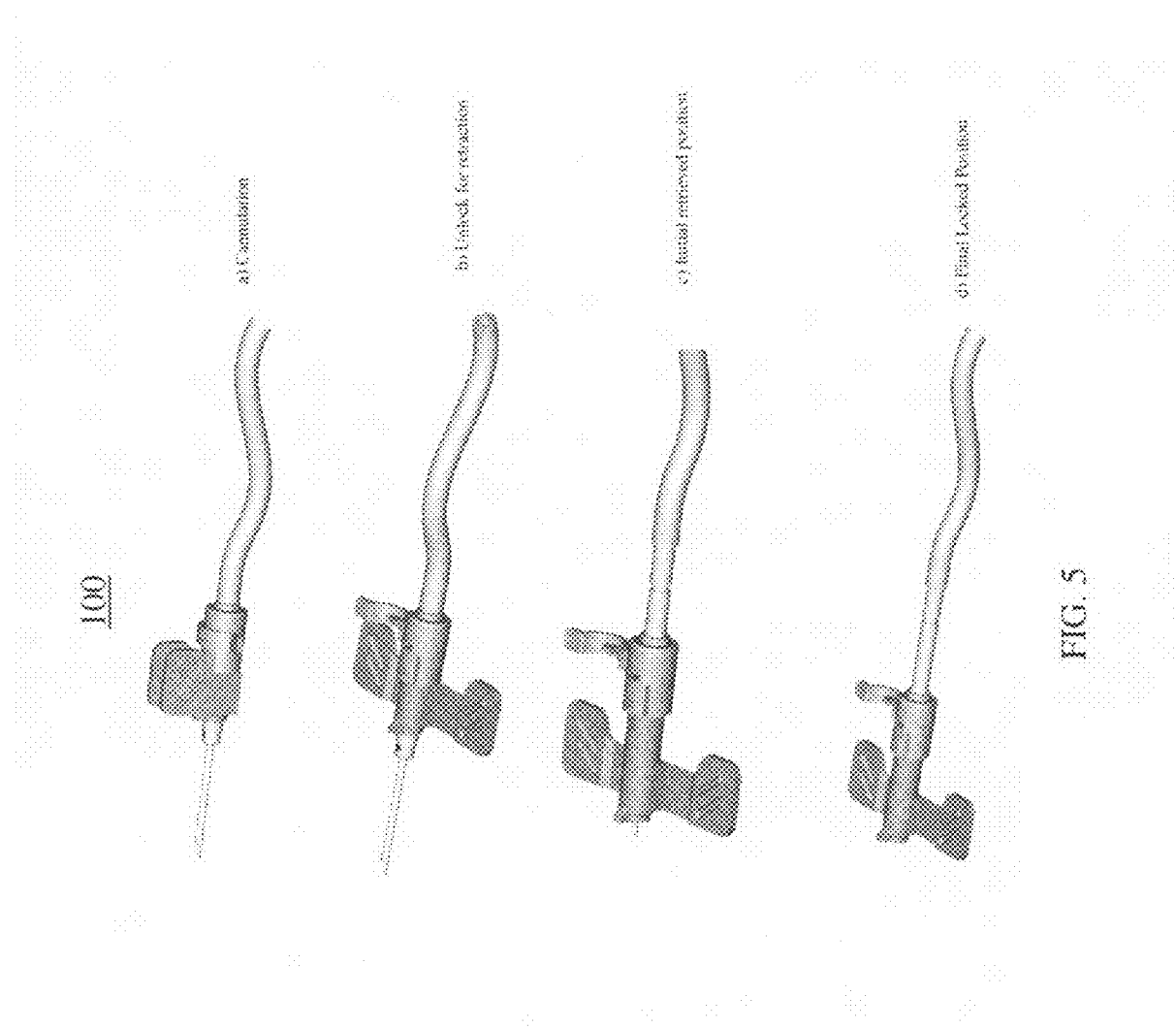

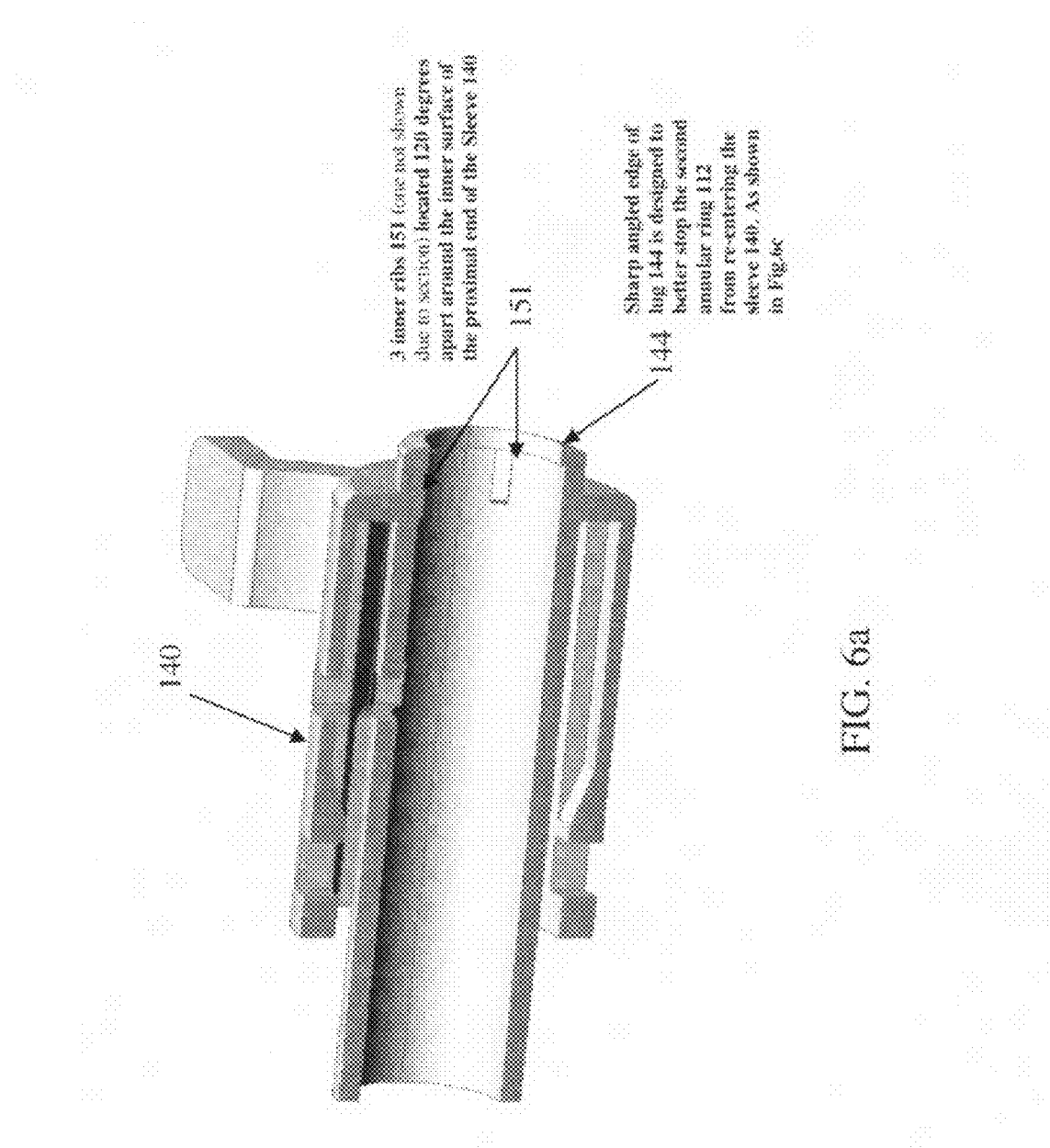

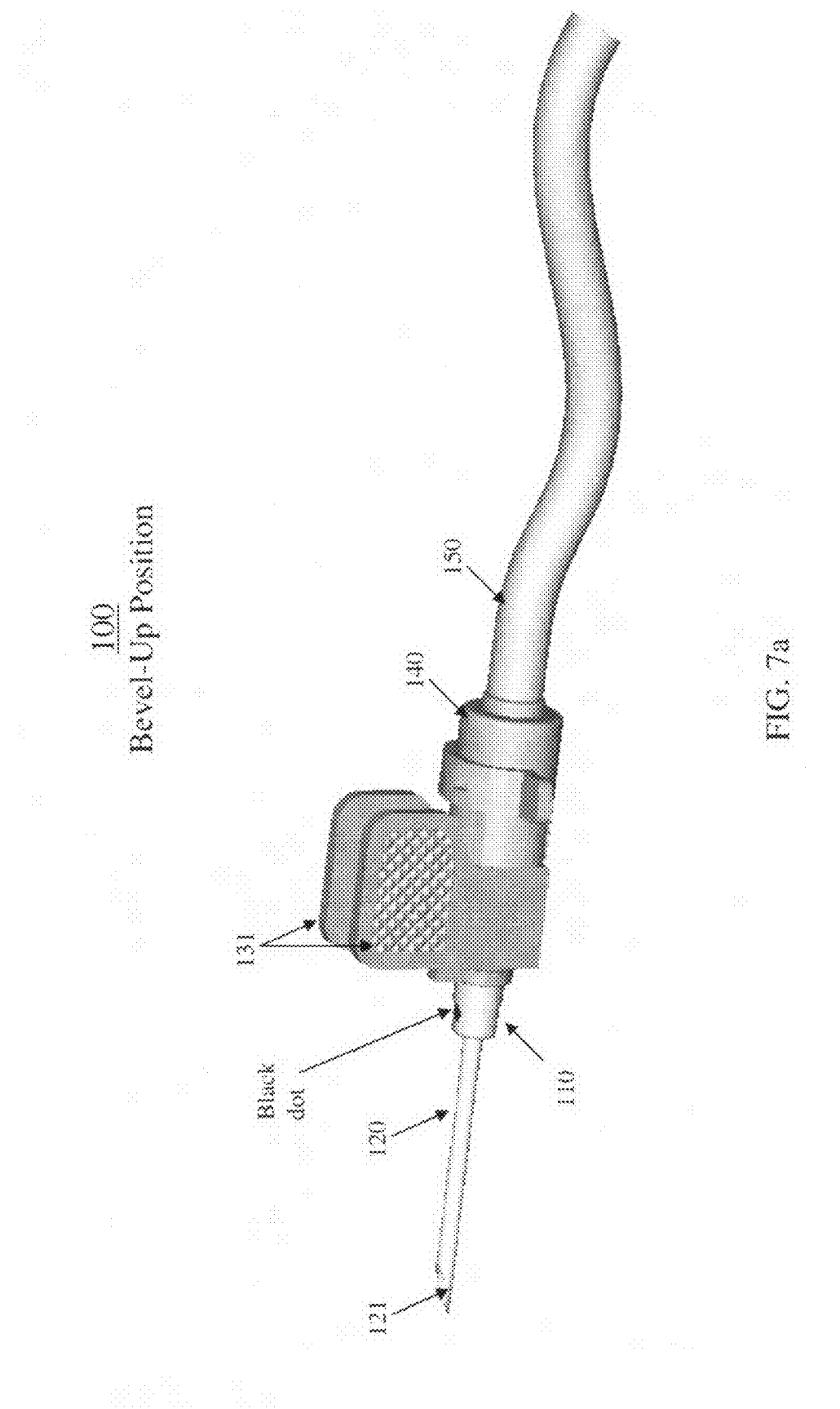

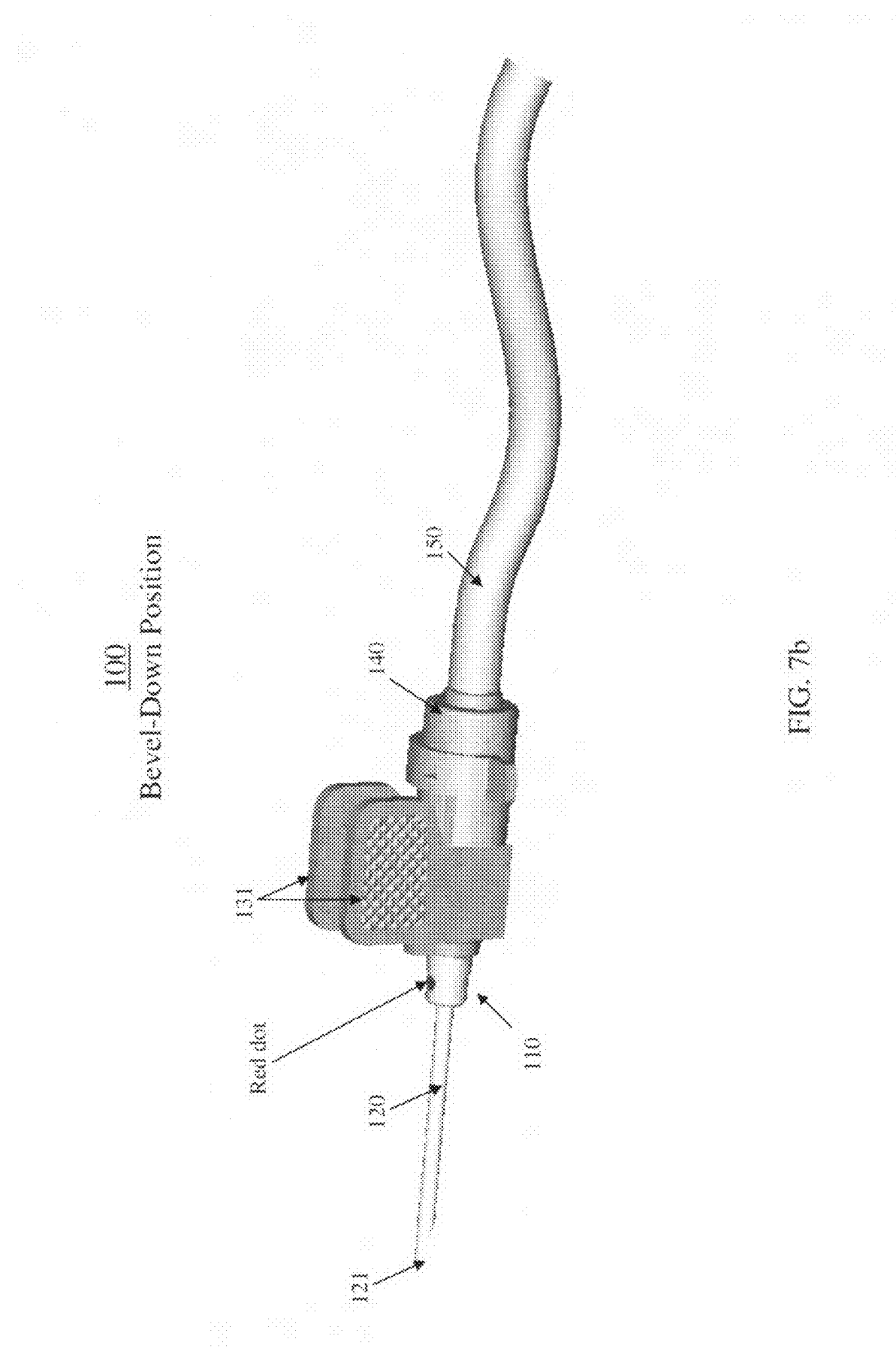

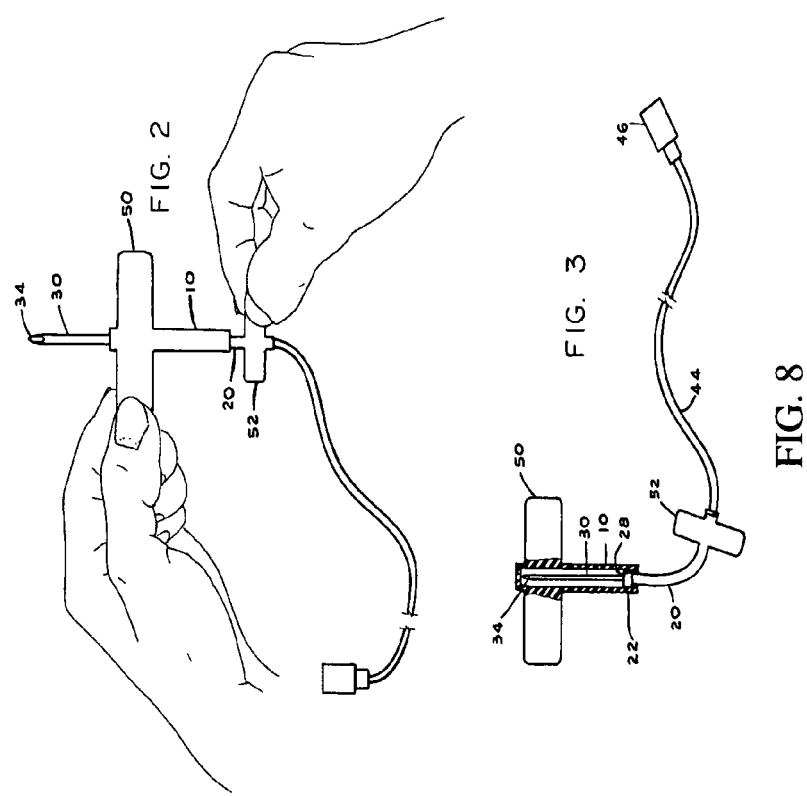

TELESCOPIC SAFETY ARTERIOVENOUS FISTULA NEEDLE

BACKGROUND OF THE INVENTION

1. Field of the Invention

The present invention relates to a winged safety needle assembly and, more particularly, to a telescopic winged safety needle assembly having a winged cylindrical sheath for preventing sticking accidents from taking place when retracting the needle into the winged cylindrical sheath. Protection of the edge of the needle is achieved by unlocking and sliding the needle along the inner wall of the winged cylindrical sheath and a sleeve.

2. Discussion of the Related Art

Needlestick injuries are intended to be avoided by proper disposal of needles. Used needles may be recapped with the same cover that originally covered the needles before use or by similar covers or tubes before the needle is discarded. This method requires movement of the hands toward the exposed needle and may promote needlestick injuries during the recapping. In addition, needles may also be disposed of by tossing them into nearby refuse containers. However, this creates danger to those who handle the refuse containers.

Winged intravenous (IV) sets are well known in the art. A typical prior art IV butterfly needle used for the insertion into blood vessels and similar passageways in the body to permit the infusion or withdrawal of sterile fluids or blood is illustrated in FIG. 8. The butterfly needle generally has a hollow needle or cannula 30, a cylindrical hub 20 holding the needle 30 at one end and connected to an IV tube 52 at the opposite end, and a cylindrical housing 10 surrounding the needle with a wing-like extension 50 extending on each side thereof.

The wings 50 are used to handle the assembly during insertion and withdrawal. For example, the wings of the needle assembly may be folded upwards around the hub to provide a gripping extension for the technician or nurse to use when attempting to insert the needle into the desired vein, artery or other passageway. The wings are also used to stabilize the device while in place by providing a broad surface area of contact with the patient which allows for taping of the device to the patient while discouraging movement, especially rotation, of the device. This assists the technician or nurse in affixing the needle to the patient during the infusion of fluids or medicants.

A problem typical of butterfly needles as just described is that when the needle is withdrawn from the vein or artery, the sharpened end, now contaminated with blood or other body fluid, remains exposed. The exposed needle can be a source of great danger to the operator or to anyone who might be pricked or scratched. Needle injuries may result in the transmission of diseases such as hepatitis, HIV, or cause other types of infection. A common solution available to the operator was to simply drop the needle and its holder into a trash receptacle. However, a danger to clean up and medical waste disposal personnel continues if the used needles are not rendered harmless in some way. Another solution is to attempt to recap the needle with a safety cover immediately after use. This, however, may in itself cause injury if the operator should accidentally stick themselves during the recapping process. In addition, caps or covers may come loose and expose the used needle.

Therefore, in order to prevent such sticking accidents various proposals have been made. One such proposal is a winged needle assembly disclosed in U.S. Pat. No. 5,505, 711 (hereinafter referred to as the '711 patent). The '711 patent describes an indwelling injector needle assembly having wings including a cannula or needle body, a hub supporting a proximal end of the needle body, a tube in fluid communication with the needle body, a cylindrical holder having a distal end from which the wings protrude, and a latching mechanism. The hub can slide along an inner periphery of the holder between a first position near the distal end of the holder and a second position near a proximal end of the holder. The latching mechanism is formed in and disposed between the hub and the holder so that the hub is inhibited from moving from the first position toward the second position, and vice versa. The needle edge can be retracted within the holder while its wings remain fixed to a patient's skin.

However, the winged needle assembly disclosed in '711 patent has several disadvantages. Use of a safety needle assembly with a longer overall length (e.g., 55 mm) results in unnecessary damage to a vessel in which the needle has been inserted. This is due to the fact that any accidental movement of an exposed hub, holder, or sheath is likely to result in unnecessary damage to a vessel from the needle. In addition, the use of a longer overall length safety needle assembly requires a larger radius loop of a profusion tube connected to the safety needle assembly which is ultimately secured (taped) to the patient, i.e., a longer assembly requires a larger loop of tubing to prevent kinking of the tube. A smaller loop of tubing helps prevent accidental movement of the assembly. The '711 Patent also discloses a non-rotating needle. Therefore the needle cannot be rotated when needed after cannulation in order to maximize blood or fluid flow to or from the vessel.

Therefore, what is needed is a telescopic winged safety needle device that provides a maximum overall length for ease of handling during insertion of the needle into a vessel, and a minimum overall length while being secured to a patient to prevent damage to the vessel. In addition, a minimized overall length of a device while being secured to a patient allows a loop of tubing to be kept to a minimum radius and secured to the patient without introducing a kink in the tube. Also, a winged safety needle device is needed that allows for rotation of the needle after cannulation in order to maximize blood or fluid flow to or from the vessel.

BRIEF DESCRIPTION OF THE DRAWINGS

FIG. 2 illustrates a locked insertion position of the Telescopic Safety AVF needle according to an embodiment of the present invention;

FIG. 3 illustrates an initial retrieved position of the Telescopic Safety AVF needle according to an embodiment of the present invention;

FIG. 4 illustrates a final locked position of the Telescopic Safety AVF needle according to an embodiment of the present invention;

FIG. 5 illustrates a cannulation procedure of the Telescopic Safety AVF needle according to an embodiment of the present invention;

FIG. 6a illustrates a cross-section view of a sleeve according to an embodiment of the present invention;

FIG. 7a illustrates a first view showing an orientation of a cannula bevel according to an embodiment of the present invention;

FIG. 7b illustrates a second view showing an orientation of a cannula bevel according to an embodiment of the present invention; and FIG. 8 illustrates a prior art intravenous butterfly needle.

DETAILED DESCRIPTION

Figure 1:
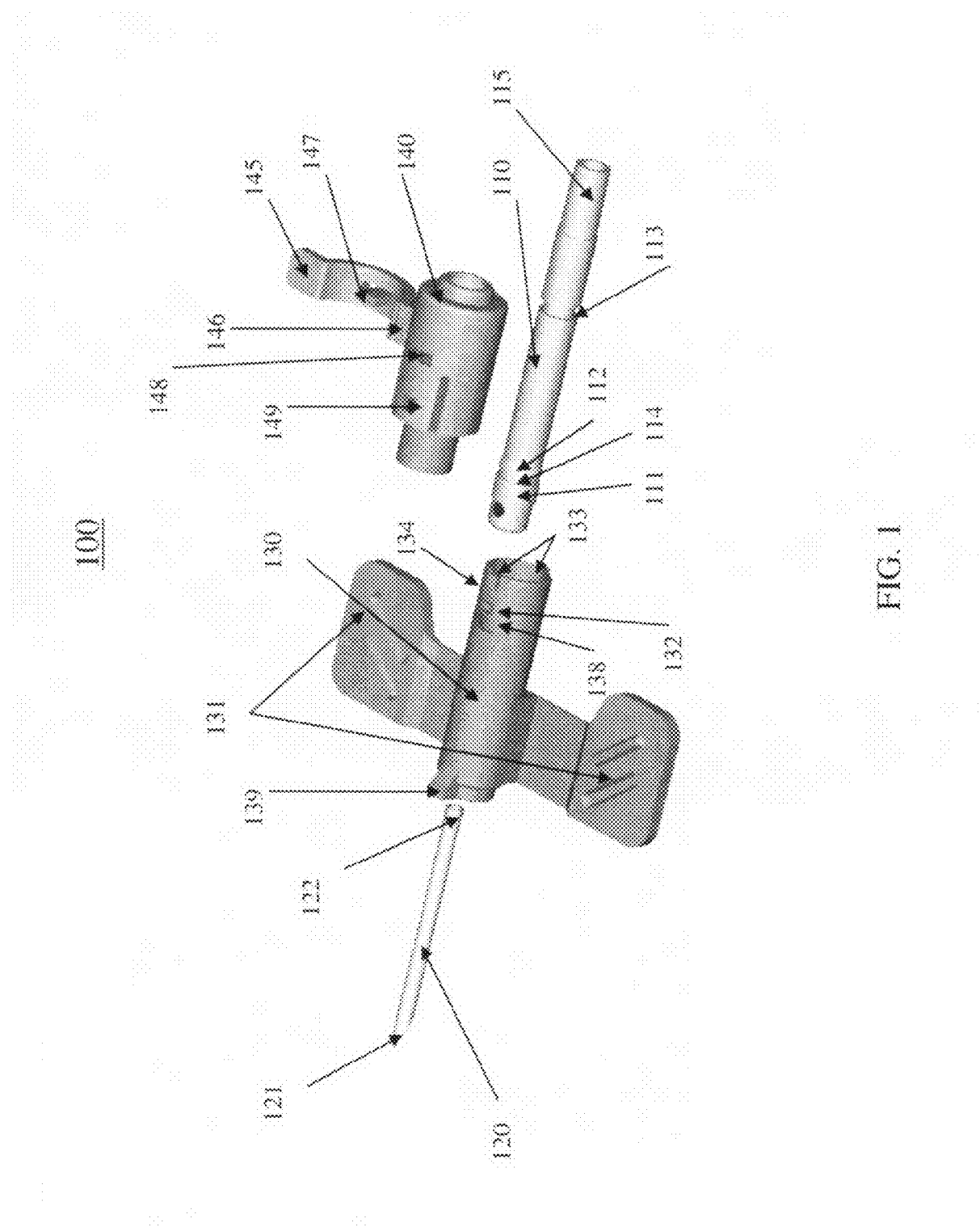
FIG. 1 illustrates an exploded view of the Telescopic Safety AVF needle according to an embodiment of the present invention.

The Telescopic Safety Arteriovenous Fistula (AVF) needle assembly 100 as shown in FIG. 1, is a telescopic retractable winged safety needle device having a needle holder 110 (hereinafter referred to as a "hub"), a needle or cannula 120, a winged sheath 130, and a sleeve 140. Referring to FIGS. 1, 2, 3, and 4, the hub 110 may be tubular in shape and may be made of a polycarbonate or other polymeric material. The hub 110 secures a proximal end of the needle or cannula 120 at the distal end. The needle or cannula 120 is hollow, has a beveled edge 121 at the distal end, and may be made of stainless steel. The base 122 or proximal portion of the hollow needle 120 is fixed to and supported by the hub 110. A tube, for example a polyvinyl chloride (PVC) tube 150, is slid over the proximal end of the hub 110, providing a fluid tight seal. The hub 110 has a stopper 115 at the proximal end for tube 150 bonding. The winged sheath 130 and sleeve 140 are axially slideable on the hub 110 to form a telescopic union of the three pieces.

The hub 110 also has two large diameter portions, a first annular ring 111 and a second annular 112, a second groove 114 near the distal end, and a first groove 113 at the proximal end.

The winged sheath 130 is a cylindrical structure with a hollow interior. The winged sheath 130 may be made of a polyethylene material. The winged sheath 130, which is axially slideable on the hub 110, has a constant inner diameter (defining the hollow interior). At the distal end of the sheath, a pair of wings 131 are positioned for use in grasping the device when squeezed together for cannulation into the patient's skin (see FIG. 5) and for adhering the device to a patient's skin during infusion, haemodialysis, apheresis, and blood collection when laying flat. The wings may be adhered to a patient using, for example, medical tape. The flexible wings 131 are integrally formed with the body of the supporting cylinder of the winged sheath 130 on both sides thereof, and the shape of the wings 131 is not particularly limited. The wings 131 are preferably provided on the cylinder body to form one plane as shown in FIG. 1-FIG. 5.

Referring to FIG. 1 and FIG. 2, the sheath 130 has two rear lugs 132, 133 located on each of the top and bottom of the exterior surface at the proximal end. A notch 134 is formed between the rear lugs 132, 133. Also at the proximal end of the sheath 130, distal of the rear lugs 132, 133 there is an opening 138 for receiving a protrusion 147 of a locking tab 145 attached to the sleeve 140 that can be selectively placed in a locked or unlocked position. The locking tab 145 has a hinge 146 attached to the side of the sleeve 140 so that when in an unlocked position, it stays attached thereto. The locking tab 145 utilizes the protrusion 147 that fits into an opening 148 in the sleeve 140 and in the opening 138 in the sheath 130 when the locking tab 145 is in the locked position. The protrusion 147 extends into the first groove 113 of the hub 110 to prevent movement of the sleeve 140 and sheath 130 with respect to the hub 110.

In the insertion position (see FIG. 2), the needle 120 is exposed through the distal end of the sheath 130 and is held in this position when the protrusion 147 of the locking tab 145 engages the first groove 113 in the hub 110 through the opening 148 in the sleeve 140 and the opening 138 in the sheath 130. In the insertion position the telescopic relationship of the sheath 130, sleeve 140, and hub 110 is such that the overall length of the Telescopic Safety AVF device 100 is minimized (e.g., 38 mm overall length). This minimized length prevents unnecessary damage to the vessel in which the needle 120 has been inserted. This is due to the fact that any accidental movement of the exposed hub 110, sleeve 140, and sheath 130 is likely to be reduced because of the overall reduced length of such an assembly relative to a longer length prior art safety needle device (e.g., 55 mm). In addition, the use of a minimized length also allows a minimized radius loop of the PVC tube 150 which is ultimately secured (taped) to the patient, i.e., a longer device requires a larger loop of tubing to prevent kinking of the tube. A smaller loop of tubing helps prevent accidental movement of the device. Therefore, a loop of PVC tube 150 may be kept to a minimum radius and secured to the patient without introducing a kink in the tube.

Referring to FIG. 3, when the needle 120 is to be withdrawn from the patient, any tape securing the wings 131 to the patient is removed. The technician then places his/her index finger against a notch 139 to hold the sheath 130 against the patient. The locking tab 145 of the sleeve 140 is disengaged and the hub 110 with the attached needle 120 are pulled in a proximal direction relative to the sheath 130 and sleeve 140 (which are no longer locked together) until the second large diameter portion (second annular ring) 112 of the hub 110 is pulled to the proximal end of the sleeve 140 and abuts against three inner ribs 151 located 120 degrees apart around the inner proximal surface of the sleeve 140.

Figure 6B:
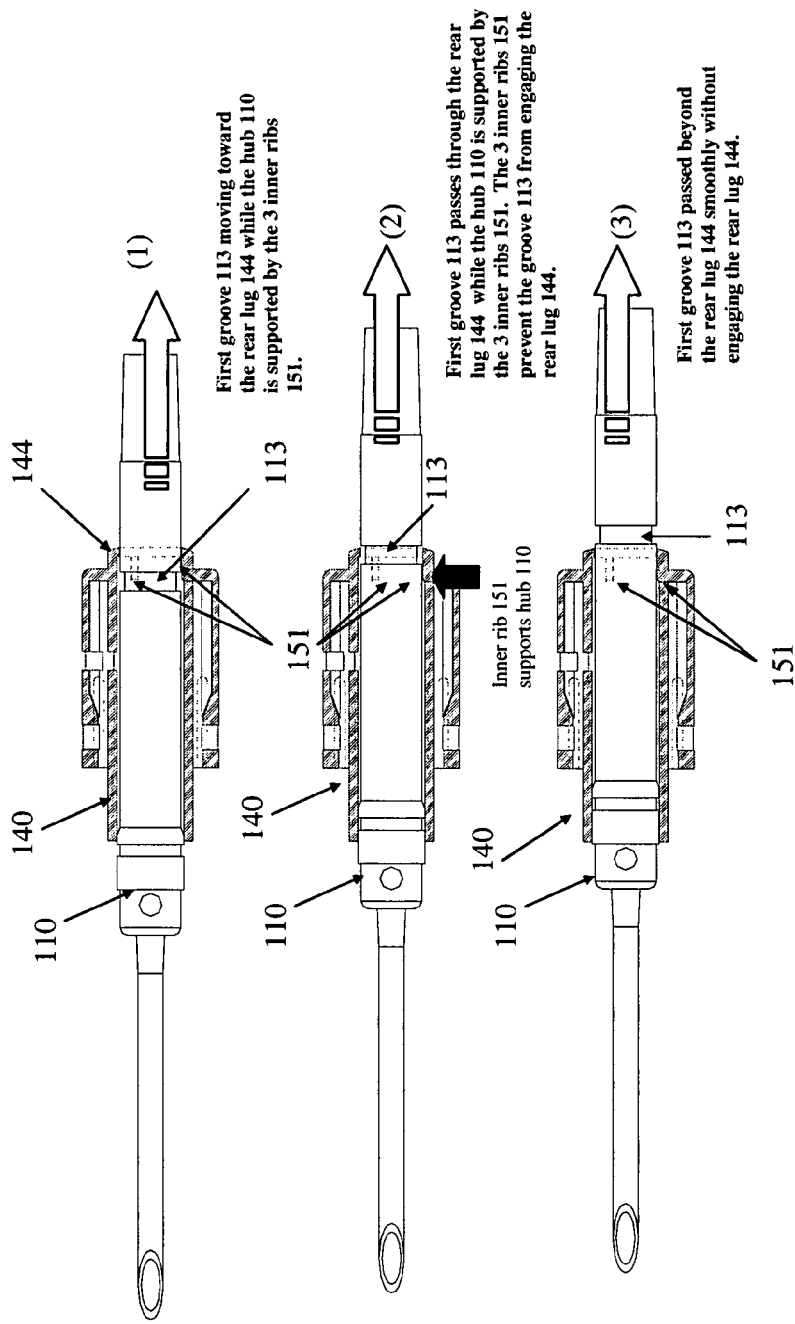
FIG. 6b illustrates three cross-section views of a hub moving relative to a sleeve according to an embodiment of the present invention.

Referring to FIG. 6a and FIG. 6b, as the first groove 113 moves in a proximal direction toward the rear lug 144, the hub 110 surface on either side of the first groove 113 is supported by the three inner ribs 151. This allows the hub 110 to pass smoothly through the proximal portion of the sleeve 140. As the first groove 113 passes through the proximal end of the sleeve and under the rear lug 144, the 3 inner ribs 151 prevent the first groove 113 from engaging the rear lug 144.

As the hub 110 continues to be drawn in the proximal direction, the sleeve 140 is now also drawn in the proximal direction due to the abutment of the second annular ring 112 with the three inner ribs 151. It should be noted that the second annular ring 112, which is aligned next to but proximal of the first annular ring 111 on the hub 110, includes a sloped surface that tapers in the proximal direction.

The hub 110 is drawn in the proximal direction until the sheath 130 is engaged in a final locking position in which the sheath 130 becomes unreleasably locked to the sleeve 140. The two rear lugs 132, 133 located on each of top and bottom of the exterior surface of the sheath 130 at the proximal end unreleasably lock with a corresponding pair of distal inner circumferential rings, interior first annular ring 142 and interior second annular ring 143, that protrude from the inner distal surface of the sleeve 140. The most proximal top and bottom lugs 133 seat in a corresponding top and bottom pair of openings 149 in the sleeve 140.

Figure 6C:
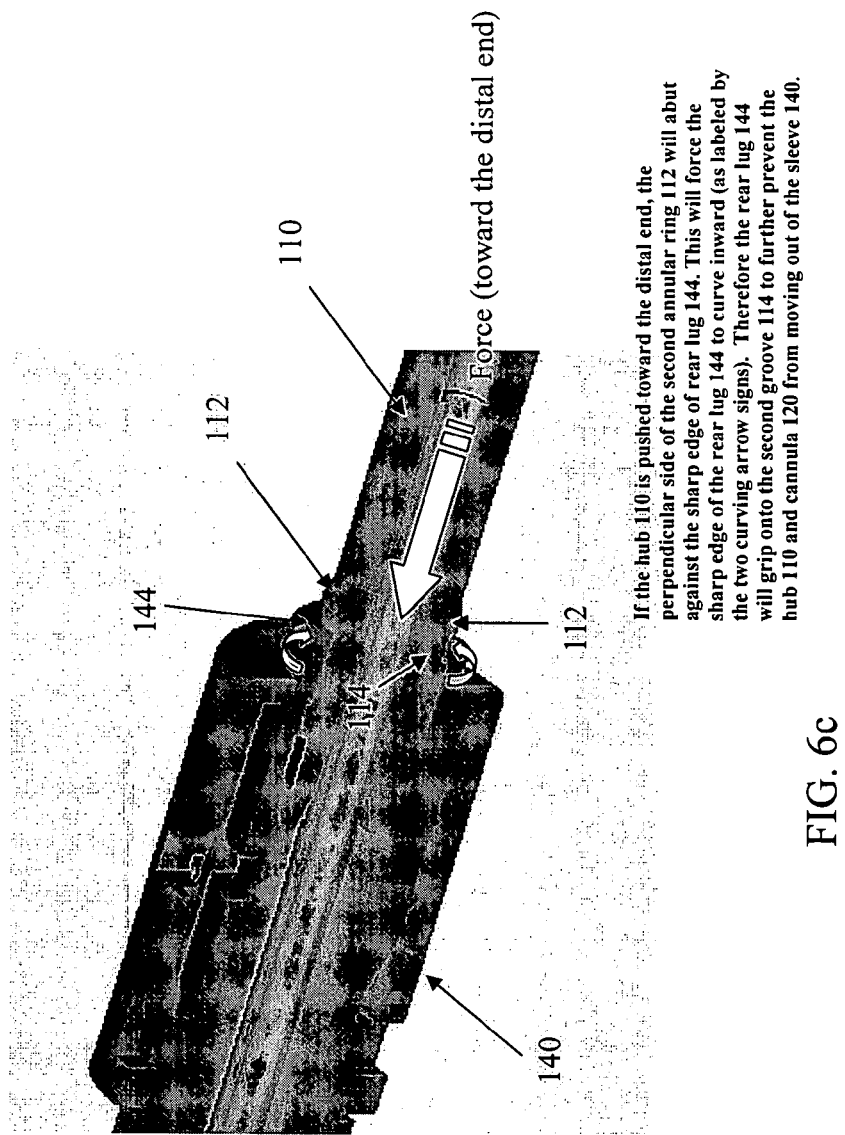
FIG. 6c illustrates a cross-section view of a sleeve and a hub in a locked position according to an embodiment of the present invention.

Next, referring to FIG. 4 and FIG. 6c, the hub 110 continues to be drawn in the proximal direction relative to the sheath 130 (locked to the sleeve 140) until the hub 110 unreleasably locks to the sleeve 140. A sharp angle shaped rear lug 144 of the sleeve 140 allows the second annular ring 112 to pass out of the sleeve 140 before the rear lug 144 seats in the second groove 114 of the hub 110. The sloped surface of the second annular ring 112 (that tapers in the proximal direction) in conjunction with the sharp angle shaped rear lug 144 of the sleeve 140 facilitates the passage of the second annular ring 112 out of the sleeve 140. The sharp angle shape of the rear lug 144 is such that the second annular ring 112 cannot re-enter the sleeve 140 past the rear lug 144. In fact, if the hub 110 is pushed in the distal direction relative to the sleeve 140, the contact between the second annular ring 112 (the distal perpendicular side of the second annular ring 112) and the sharp angle shaped rear lug 144 of the sleeve 140 will tend to cause the angle shaped rear lug 144 to curve inward, i.e., bend from being pushed by the second annular ring 112. Therefore, the rear lug 144 will grip onto the second groove 114 to further prevent the hub 110 and cannula 120 from moving distally out of the sleeve 140.

The needle 120 has now been withdrawn from the patient. Also note that the locking tab 135 is used only for maintaining the locked relationship between the sheath 130 and hub 110 in the insertion position and not in the protection position.

Referring to FIG. 7a and FIG. 7b, the Telescopic Safety AVF needle assembly 100 also includes a rotational feature that allows the hub 110 with attached needle or cannula 120 to rotate 360 degrees within the winged sheath 130. This feature allows the cannula bevel 121 orientation within the fistula or graft to be adjusted and ascertained. A black dot mark on the distal exterior surface of the hub 110 is visible when facing up (see FIG. 7a) and indicates the cannula bevel 121 is facing up within the fistula or graft. Alternatively, a red dot mark on the distal exterior surface of the hub 110 is visible when facing up (see FIG. 7b) and indicates the cannula bevel 121 is facing down within the fistula or graft. Therefore, the handling of the Telescopic Safety AVF needle assembly 100 of the present invention is simplified, since after inserting the needle 120 with the beveled surface 121 facing up into a blood vessel (the black dot on the distal exterior surface of the hub 110 is visible when facing up as shown in FIG. 7a), the beveled edge 121 is then made to face down by simply rotating the hub 110 until the red dot on the distal exterior surface of the hub 110 is visible when facing up and the needle 120 is then retained in that state (see FIG. 7b). The ability to adjust the orientation (0-360 degrees) of the cannula bevel 121 within a vessel allows a technician to adjust for maximum fluid flow.

In contrast, some prior art winged retention needles have the disadvantage that the operation thereof is troublesome, since a hollow needle is directly fixed to a winged portion with the edge surface faced up and accordingly the edge surface must be faced down by a half rotation of the entire winged needle assembly after insertion into blood vessels.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A telescopic winged safety needle assembly, comprising:
   a hub having a distal end, a proximal end, and an axial through hole;
   a cannula joined to said hub adjacent the distal end of the hub;
   a cylindrical sleeve having a locking tab attached thereto, said cylindrical sleeve being axially disposed on said hub;
   a cylindrical sheath for retaining said hub therein and having a distal end and a proximal end, said hub being slidable along an inner surface of said cylindrical sheath and an inner surface of said cylindrical sleeve from a first telescopic position at which the distal end of said cannula joined to said hub projects beyond the distal end of said cylindrical sheath by a predetermined length, to a second telescopic position at which said distal end of the cannula is protectively contained within said cylindrical sheath,
   said cylindrical sleeve being axially disposed on said proximal end of said cylindrical sheath;
   a pair of flexible wings provided on the outer peripheral surface adjacent the distal end of said cylindrical sheath; and
   a first locking mechanism and a second locking mechanism disposed on said assembly, said first locking mechanism releasably locks said hub, said cylindrical sleeve, and said sheath at the first telescopic position, and said second locking mechanism unreleasably locks said hub, said cylindrical sleeve, and said cylindrical sheath at the second telescopic position, wherein said second locking mechanism comprises a first annular ring and a second annular ring provided on the exterior distal end of said hub, an annular ring provided on the interior proximal end of said cylindrical sleeve, a first lug and a second lug provided on the proximal exterior end of said cylindrical sheath, and a first annular ring and a second annular ring provided on the interior distal end of said cylindrical sleeve, wherein when said hub, said cylindrical sleeve, and said cylindrical sheath are located at the second telescopic position, said first annular ring and said second annular ring provided on the exterior distal end of said hub unreleasably engage said annular ring provided on the interior proximal end of said cylindrical sleeve, and said first lug and said second lug provided on the proximal exterior end of said cylindrical sheath unreleasably engage said first annular ring and said second annular ring provided on the interior distal end of said cylindrical sleeve.

2. A telescopic winged safety needle assembly according to claim 1, wherein said first locking mechanism comprises said locking tab attached to said cylindrical sleeve, a first opening located along a length of the cylindrical sleeve, a second opening located on said cylindrical sheath, and a first groove formed in said hub, wherein when said hub is located at the first telescopic position in relation to said cylindrical sleeve and said cylindrical sheath, said locking tab releasably engages said hub, said cylindrical sleeve, and said cylindrical sheath.

3. A telescopic winged needle assembly according to claim 2, wherein said locking tab includes a projection that is inserted through the first opening in the cylindrical sleeve and the second opening in the cylindrical sheath to releasably engage said first groove of said hub, said cylindrical sleeve, and said cylindrical sheath.

4. A telescopic winged safety needle assembly according to claim 3, wherein said annular ring provided on the interior proximal end of said cylindrical sleeve includes a sharp angled edge to unreleasably engage said second annular ring provided on the exterior distal end of said hub.

5. A telescopic winged safety needle assembly according to claim 1, wherein said cannula is rotatable relative to the cylindrical sheath.

6. A telescopic winged safety needle assembly according to claim 5, wherein said hub is marked to indicate the orientation of a bevel edge of the cannula relative to the cylindrical sheath.

7. A telescopic winged needle assembly according to claim 1, wherein a tube is connected to the proximal end of the hub.

8. A telescopic winged needle assembly according to claim 1, wherein an outer surface of said hub is supported by three inner ribs located on an inner proximal surface of the cylindrical sleeve to allow the hub to pass smoothly through the inner proximal surface of the cylindrical sleeve.

9. A telescopic winged needle assembly according to claim 1, wherein the locking tab is attached to the cylindrical sleeve by a hinge.

10. A telescopic winged safety needle assembly, comprising:
   a hub having a distal end, a proximal end, and an axial through hole;
   a cannula joined to said hub adjacent the distal end of the hub;
   a cylindrical sleeve having a locking tab attached thereto, said cylindrical sleeve being axially disposed on said hub;
   a cylindrical sheath for retaining said hub therein and having a distal end and a proximal end, said hub being slidable along an inner surface of said cylindrical sheath and an inner surface of said cylindrical sleeve from a first telescopic position at which the distal end of said cannula joined to said hub projects beyond the distal end of said cylindrical sheath by a predetermined length, to a second telescopic position at which said distal end of the cannula is protectively contained within said cylindrical sheath and said assembly is maximized in length, said cannula joined to said hub being rotatable relative to said cylindrical sleeve and said cylindrical sheath;
   a pair of flexible wings provided on the outer peripheral surface adjacent the distal end of said cylindrical sheath; and
   a first locking mechanism and a second locking mechanism disposed on said assembly, whereby said first locking mechanism releasably locks said hub, said cylindrical sleeve, and said cylindrical sheath at the first telescopic position, and said second locking mechanism unreleasably locks said hub, said cylindrical sleeve, and said cylindrical sheath at the second telescopic position, wherein said second locking mechanism comprises a first annular ring and a second annular ring provided on the exterior distal end of said hub, an annular ring provided on the interior proximal end of said cylindrical sleeve, a first lug and a second lug provided on the proximal exterior end of said cylindrical sheath, and a first annular ring and a second annular ring provided on the interior distal end of said cylindrical sleeve, wherein when said hub, said cylindrical sleeve, and said cylindrical sheath are located at the second telescopic position, said first annular ring and said second annular ring provided on the exterior distal end of said hub unreleasably engage said annular ring provided on the interior proximal end of said cylindrical sleeve, and said first lug and said second lug provided on the proximal exterior end of said cylindrical sheath unreleasably engage said first annular ring and said second annular ring provided on the interior distal end of said cylindrical sleeve.

11. A telescopic winged safety needle assembly according to claim 10, wherein said first locking mechanism comprises said locking tab attached to said cylindrical sleeve, a first opening located along a length of the cylindrical sleeve, a second opening located on said cylindrical sheath, and a first groove formed in said hub, wherein when said hub is located at the first telescopic position in relation to said cylindrical sleeve and said cylindrical sheath, said locking tab releasably engages said hub, said cylindrical sleeve, and said cylindrical sheath.

12. A telescopic winged safety needle assembly according to claim 10, wherein said annular ring provided on the interior proximal end of said cylindrical sleeve includes a sharp angled edge to unreleasably engage said second annular ring provided on the exterior distal end of said hub.

13. A telescopic winged safety needle assembly according to claim 10, wherein said hub is marked to indicate the orientation of a bevel edge of the cannula relative to the cylindrical sheath.

14. A telescopic winged needle assembly according to claim 10, wherein said locking tab includes a projection that is inserted through the first opening in the cylindrical sleeve and the second opening in the cylindrical sheath to releasably engage said first groove of said hub, said cylindrical sleeve, and said cylindrical sheath.

15. A telescopic winged needle assembly according to claim 10, wherein an outer surface of said hub is supported by three inner ribs located on an inner proximal surface of the cylindrical sleeve to allow the hub to pass smoothly through the inner proximal surface of the cylindrical sleeve.

16. A telescopic winged needle assembly according to claim 10, wherein a tube is connected to the proximal end of the hub.

17. A telescopic winged needle assembly according to claim 10, wherein the locking tab is attached to the cylindrical sleeve by a hinge.

18. A telescopic winged safety needle assembly, comprising:
   a hub having a distal end, a proximal end, and an axial through hole;
   a cannula joined to said hub adjacent the distal end of the hub;
   a cylindrical sleeve axially disposed on said hub;
   a cylindrical sheath for retaining said hub therein and having a distal end and a proximal end, said hub being slidable along an inner surface of said cylindrical sheath and an inner surface of said cylindrical sleeve from a first telescopic position at which the distal end of said cannula joined to said hub projects beyond the distal end of said cylindrical sheath by a predetermined length and said assembly is minimized in length, to a second telescopic position at which said distal end of the cannula is protectively contained within said cylindrical sheath and said assembly is maximized in length;
   a first locking mechanism and a second locking mechanism disposed on said assembly, said first locking mechanism releasably locks said hub, said cylindrical sleeve, and said sheath at the first telescopic position, and said second locking mechanism unreleasably locks said hub, said cylindrical sleeve, and said cylindrical sheath at the second telescopic position, said hub is pulled in a proximal direction relative to said cylindrical sheath and said cylindrical sleeve at said first telescopic position until said cylindrical sheath unreleasably locks to said cylindrical sleeve, followed by said hub unreleasably locking to said cylindrical sleeve at said second telescopic position, wherein said second locking mechanism comprises a first annular ring and a second annular ring provided on the exterior distal end of said hub, an annular ring provided on the interior proximal end of said cylindrical sleeve, a first lug and a second lug provided on the proximal exterior end of said cylindrical sheath, and a first annular ring and a second annular ring provided on the interior distal end of said cylindrical sleeve, wherein when said hub, said cylindrical sleeve, and said cylindrical sheath are located at the second telescopic position, said first annular ring and said second annular ring provided on the exterior distal end of said hub unreleasably engage said annular ring provided on the interior proximal end of said cylindrical sleeve, and said first lug and said second lug provided on the proximal exterior end of said cylindrical sheath unreleasably engage said first annular ring and said second annular ring provided on the interior distal end of said cylindrical sleeve and a pair of flexible wings provided on the outer peripheral surface adjacent the distal end of said cylindrical sheath.

19. A telescopic winged safety needle assembly according to claim 18, further including a first locking mechanism and a second locking mechanism disposed on said assembly, whereby said first locking mechanism releasably locks said hub, said cylindrical sleeve, and said sheath at the first telescopic position, and said second locking mechanism unreleasably locks said hub, said cylindrical sleeve, and said cylindrical sheath at the second telescopic position.

20. telescopic winged safety needle assembly according to claim 19, wherein said first locking mechanism comprises a locking tab attached to said cylindrical sleeve, a first opening located along a length of the cylindrical sleeve, a second opening located on said cylindrical sheath, and a first groove formed in said hub, wherein when said hub is located at the first telescopic position in relation to said cylindrical sleeve and said cylindrical sheath, said locking tab releasably engages said hub, said cylindrical sleeve, and said cylindrical sheath.

21. A telescopic winged needle assembly according to claim 20, wherein said locking tab includes a projection that is inserted through the first opening in the cylindrical sleeve and the second opening in the cylindrical sheath to releasably engage said first groove of said hub, said cylindrical sleeve, and said cylindrical sheath.

22. A telescopic winged needle assembly according to claim 20, wherein the locking tab is attached to the cylindrical sleeve by a hinge.

23. A telescopic winged safety needle assembly according to claim 18, wherein said annular ring provided on the interior proximal end of said cylindrical sleeve includes a sharp angled edge to unreleasably engage said second annular ring provided on the exterior distal end of said hub.

24. A telescopic winged safety needle assembly according to claim 17, wherein said cannula is rotatable relative to the cylindrical sheath.

25. A telescopic winged safety needle assembly according to claim 24, wherein said hub is marked to indicate the orientation of a bevel edge of the cannula relative to the cylindrical sheath.

26. A telescopic winged needle assembly according to claim 18, wherein a tube is connected to the proximal end of the hub.

27. A telescopic winged needle assembly according to claim 18, wherein an outer surface of said hub is supported by three inner ribs located on an inner proximal surface of the cylindrical sleeve to allow the hub to pass smoothly through the inner proximal surface of the cylindrical sleeve.

* * * * *